United States Patent
Grodzins et al.

(10) Patent No.: US 6,459,761 B1
(45) Date of Patent: Oct. 1, 2002

(54) SPECTRALLY SHAPED X-RAY INSPECTION SYSTEM

(75) Inventors: Lee Grodzins, Lexington, MA (US); Peter Rothschild, Chestnut Hill, MA (US)

(73) Assignee: American Science and Engineering, Inc., Billerica, MA (US)

(*) Notice: Subject to any disclaimer, the term of this patent is extended or adjusted under 35 U.S.C. 154(b) by 0 days.

(21) Appl. No.: 09/502,093

(22) Filed: Feb. 10, 2000

(51) Int. Cl.⁷ .............................................. G01N 23/06
(52) U.S. Cl. ........................................ 378/57; 378/56
(58) Field of Search ........................... 378/57, 56, 90, 378/87, 86

(56) References Cited

U.S. PATENT DOCUMENTS

| | | | |
|---|---|---|---|
| 3,748,487 A | 7/1973 | Edholm et al. ............... 250/512 |
| 3,919,467 A | 11/1975 | Peugeot ...................... 178/6.8 |
| 5,040,199 A | 8/1991 | Stein ........................... 378/56 |
| 5,394,454 A | 2/1995 | Harding ....................... 378/86 |
| 5,600,700 A | 2/1997 | Krug et al. ................... 378/57 |
| 5,768,334 A | 6/1998 | Maitrejean et al. ........... 378/53 |
| 5,805,660 A | * 9/1998 | Perion et al. ................. 378/53 |
| 5,838,759 A | * 11/1998 | Armistead .................... 378/57 |
| 5,940,460 A | * 8/1999 | Huang et al. ................. 378/57 |
| 5,940,468 A | * 8/1999 | Huang et al. ................. 378/57 |

FOREIGN PATENT DOCUMENTS

| | | | |
|---|---|---|---|
| WO | WO97/18462 | 5/1997 | G01N/23/04 |
| WO | WO 99/09400 | 2/1999 | G01N/23/08 |
| WO | WO99/33064 | 7/1999 | G21K/5/10 |
| WO | WO99/39189 | 8/1999 | G01N/23/04 |
| WO | WO 00/33060 | 6/2000 | |

OTHER PUBLICATIONS

U.S. patent application Ser. No. 09/395,331, filed Sep. 13, 1999.

\* cited by examiner

*Primary Examiner*—Robert H. Kim
*Assistant Examiner*—Irakli Kiknadze
(74) *Attorney, Agent, or Firm*—Bromberg & Sunstein LLP

(57) ABSTRACT

A system and methods for non-invasive x-ray inspection of an enclosure in such a manner as to reduce the ambient radiation dose to below a specified level. A beam spectrally filtered to emphasize a high-energy component of penetrating radiation is interleaved, temporally, with a beam dominated by a low-energy component. Thus both lightly loaded and heavily loaded cargo may be inspected while limiting the ambient scattered radiation.

8 Claims, 4 Drawing Sheets

US 6,459,761 B1

SPECTRALLY SHAPED X-RAY INSPECTION SYSTEM

TECHNICAL FIELD

The present invention relates to systems and methods for inspecting objects, particularly cargo in containers, trucks and trains, using spectrally filtered penetrating radiation.

BACKGROUND OF THE INVENTION

X-ray inspection of containers is well established for many purposes including the search for contraband, stolen property and the verification of the contents of shipments that cross national borders.

Such inspection systems typically produce a so-called transmission image by measuring the intensity distribution of the x-rays that traverse the container. The contents of lightly loaded containers can be effectively examined with x-ray energies in the hundreds of keV range but heavily loaded semi-trailers, tanker trucks, trains, and ISO containers typically require beams of x-rays in the MeV range. The design of an x-ray inspection system to examine heterogeneous cargo requires joint consideration of conflicting requirements for penetration, sensitivity and radiation dosage, for which the following first-order criteria give general guidance.

Penetration: As the energy of the x-rays increases, with the electron beam power kept constant, the penetration increases inversely with the linear absorption coefficient, $\lambda$ cm$^{-1}$. For example, the high-energy x-ray components of the beam from a 3 MeV accelerator penetrate approximately 3 times farther through iron than do the high-energy components from a 450 keV x-ray generator; the relevant linear absorption coefficients in iron decrease by almost that factor of 3.

Sensitivity: The sensitivity of the x-rays to a given thickness $\Delta x$ of an object depends on the material surrounding the object as well as the material of the object itself. Other parameters being equal, the sensitivity S is usefully defined as the fractional change in the count rate I per centimeter of the material. That is, $$S = \frac{\Delta I / I}{\Delta x} = -\lambda,$$

where $\Delta I$ is the decrement in count rate due to material of thickness $\Delta x$. The sensitivity is greatest at the lowest energy (highest value of $\lambda$) of penetrating radiation. In the above example, the sensitivity of the high energy x-rays has fallen by a factor of almost 3 on increasing the energy from 450 keV to 3 MeV, and it takes almost 9 times as many x-rays to obtain the same statistical accuracy for the measured attenuation.

The conflict between penetration and sensitivity is generally met by accepting the full spectrum of x-rays generated by the electron beam. The high energy components are effective for maximum penetration while the far more copious lower energy components have the sensitivity needed to most effectively examine lightly loaded containers or containers with lightly loaded sections.

Radiation dose: The radiation dose in a beam of x-rays generated by an electron of energy E striking a tungsten target is approximately proportional to E$^3$, as discussed by Buechner, et al., *Physical Review*, vol. 74, pp. 1348ff, (1948). At constant power, the direct radiation dose in the beam varies approximately as E$^2$, as does the ambient radiation dose. As used in this description and in any appended claims, the term "ambient radiation dose" refers to the dose in the surroundings from scattered radiation.

In the example above, with the electron power kept constant, the ambient radiation dose rises by almost a factor of 40 as the electron energy is raised from 450 keV to 3 MeV. In order to satisfy the radiation safety codes it becomes necessary to add costly shielding that generally involve strengthened infrastructure and massive doors to the inspection area. In the United States, the inspection system must keep the dose to areas accessible to people to less than 5 $\mu$Sv/hr. (21 CFR §1020.40) These specifications are referred to as "cabinet" specifications. The phrase "open cabinet" as used herein refers to an enclosure, with or without doors or roof, that meets legal cabinet regulation specifications without the need for radiation shields other than in the vicinity of the beam.

To meet the demands of inspecting densely-loaded cargo, some current systems apply x-rays of energy higher than 450 keV. It has been assumed and taught in the art that higher energy results in high ambient radiation that requires extensive shielding and greatly increased costs to comply with regulations.

Some currently employed cargo inspection systems use pulsed linear accelerators (linacs) operating in the range from about 3 MeV to 9 MeV, producing fan beams of x-rays that pass through the cargo into a linear array of x-ray detectors that measure their intensity. The copious low energy components of the fan beam produce high quality images of lightly loaded containers while the high-energy components have sufficient penetrating power to find contraband behind more than 30 cm of steel. The radiation produced by the linacs is very high, typically greater than 1 Gray/min at a meter, and so too is the cost for the radiation enclosure and shielding required. The cost of the building, with radiation-containing doors for the inspection tunnel often exceeds the cost of the x-ray inspection system itself.

Current uses of spectrally selective absorbers in the context of x-ray beam generation include their use in MeV x-ray generators to flatten the intensity distribution as a function of angle. Absorbers are also used in medical applications to minimize the radiation dose to the patient by eliminating the low-energy components that are absorbed preferentially in the skin and near-surface tissues and play no useful role in the diagnosis or treatment. Finally, absorbers are used to create quasi-monochromatic beams of x-rays, as for dual-energy analysis, for example. Ambient radiation, as defined above, figures in none of these instances of current use of absorbers, neither as a design consideration nor to provide active control of the x-ray intensities.

SUMMARY OF THE INVENTION

In accordance with systems and methods described herein, both the high energy and low-energy components of MeV x-ray generators may be used while keeping the ambient radiation low enough so that the cost of the infrastructure to contain the radiation is significantly reduced. Thus, the seemingly mutually exclusive needs for penetration and sensitivity to easily penetrable objects may advantageously be obtained. This may be accomplished, in accordance with the present invention, by combining several modalities: First, a highly penetrating, high-energy x-ray beam with minimal ambient radiation can be obtained by properly shaping the spectrum of the x-ray beam from the accelerator by means of an appropriate absorber. Second, the essential lower-energy x-ray spectrum, generated by the same or a different accelerator, can satisfy the needs for sensitivity to easily penetrable objects while maintaining minimal ambient radiation. Third, the two spectra can be coordinated in time so that there is no interference or cross-talk between the two components. Additional embodiments of the invention also make use of the fact that the intensities of the x-ray generators can be controlled to maximize the effectiveness of the inspection system while maintaining "open cabinet" status. One method of control uses the low energy transmission system to control the intensity of the beams from the high energy transmission system; another method of control, which can be used in conjunction with the first, uses ambient radiation monitors to control the x-ray intensities from the x-ray generators.

BRIEF DESCRIPTION OF THE DRAWINGS

The foregoing features of the invention will be more readily understood by reference to the following detailed description taken with the accompanying drawings.

DETAILED DESCRIPTION OF THE SPECIFIC EMBODIMENTS

Systems for advantageously reducing the dose of ambient radiation exposure yet providing the advantages of a highly penetrating x-ray beam are now described. A common theme in various embodiments described below is the interleaving a low-intensity, predominantly low-energy x-ray spectrum with a low-intensity, predominantly high energy spectrum.

Figure 1:
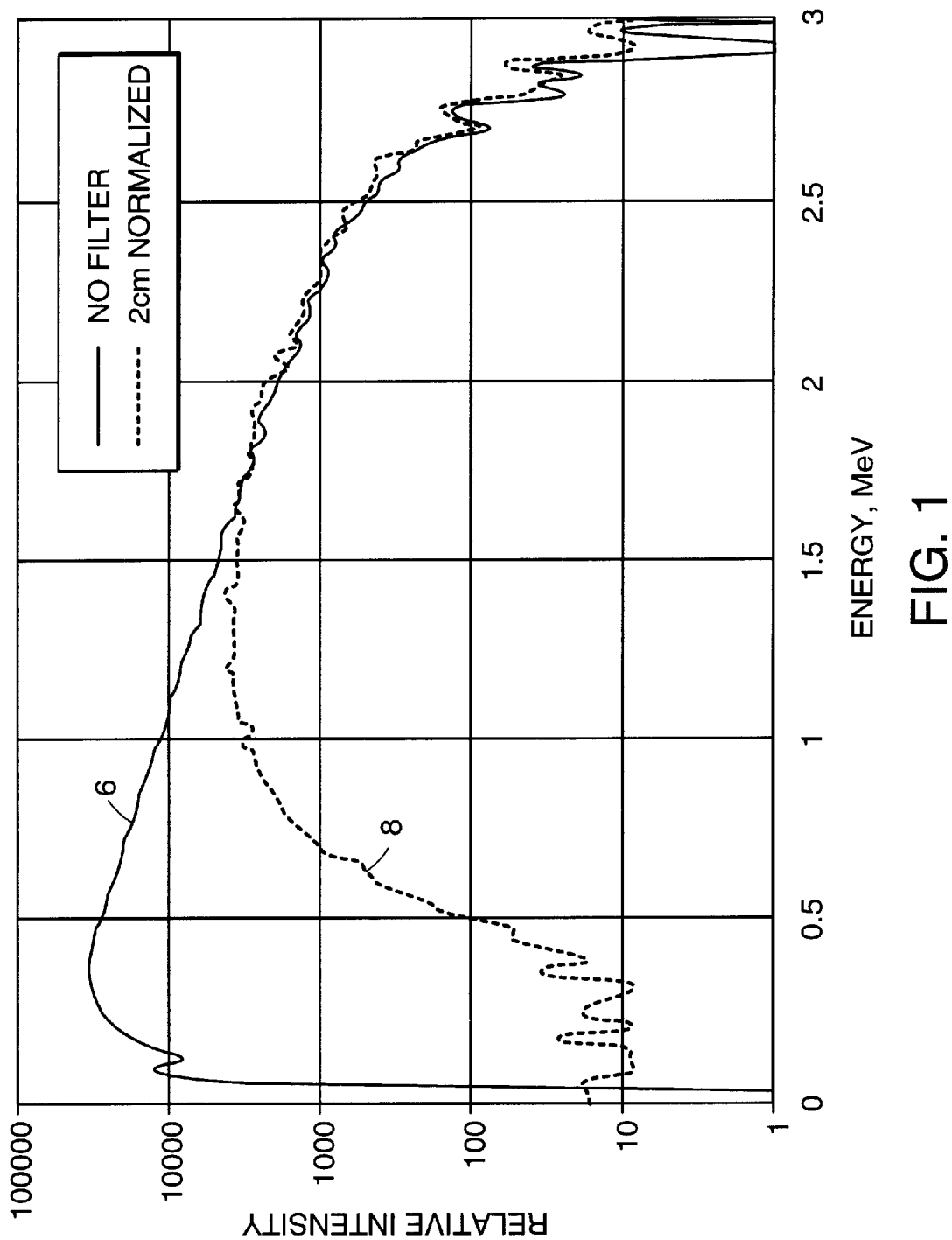
FIG. 1 shows Monte-Carlo-simulated spectra of x-rays emitted at 90° from a tungsten target bombarded with 3 MeV electrons, prior to filtering and subsequent to filtering in accordance with a preferred embodiment of the present invention.

Referring first to FIG. 1, spectra are shown of x-rays emitted at 90° from a tungsten target bombarded with 3 MeV electrons. The solid line, designated by numeral 6, corresponds to the spectrum, generated by Monte Carlo simulation, of the x-rays emitted under the specified condition. Unfiltered spectrum 6 is shown, on a logarithmic scale, as a function of photon energy, in MeV. (While refered to herein as "unfiltered", solid curve 6 has in fact been lightly filtered to reduce the intensity of x-rays below about 200 keV.) In unfiltered spectrum 6, approximately 50% of the x-rays have energies below 500 keV and only 8% of the x-rays have energies above 1.5 MeV. Thus, the unfiltered spectrum may be characterized by referring to a fiducial energy, here 500 keV, below which half the emitted photons, by number, have their energy.

Dashed curve 8 is the intensity distribution of emitted x-rays (to within a multiplicative factor), as filtered through 2 cm of uranium and thereby 'hardened'. Two cm of uranium corresponds to approximately 2.2 mean free paths for the higher x-ray energies shown in the figure. The less penetrating radiation, at energies below about 400 keV, have been absorbed by four orders of magnitude, while the penetrating components have been decreased by less than one order of magnitude. A 2-cm thick absorber of depleted uranium placed in the beam almost eliminates the x-rays below about 700 keV. The filtered radiation may thus be characterized as dominated by photons above a specified fiducial energy.

Figure 2A:
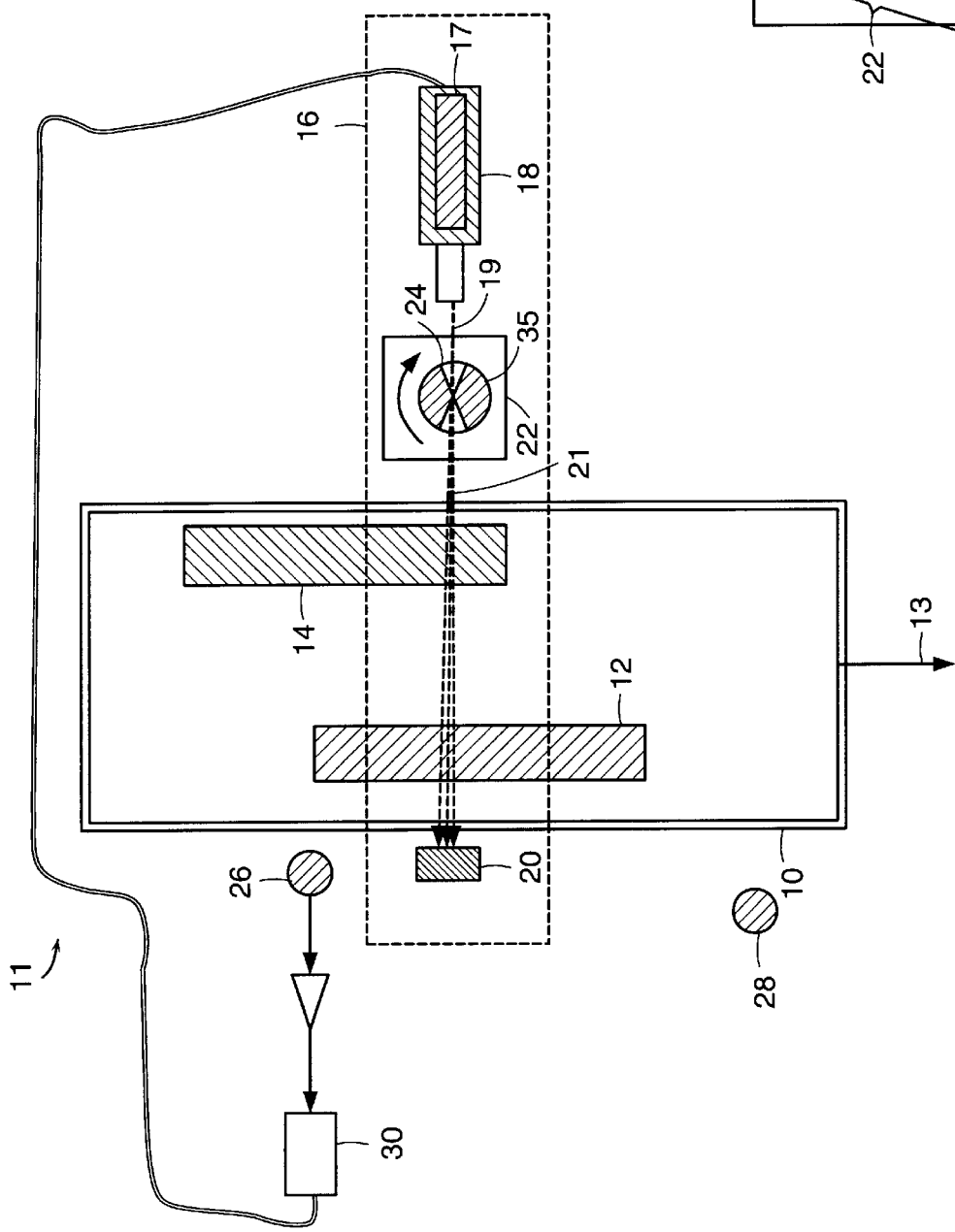
FIG. 2a is a schematic top view of a transmission imaging inspection system using a single, pulsed high-energy x-ray generator to produce both a low energy and a high energy transmission image in accordance with preferred embodiment of the present invention.

The present invention, in preferred embodiments, achieves an advantageous reduction in radiation exposure by virtue of filtering as now described with reference to FIGS. 2–4. A schematic top view of an x-ray inspection system, designated generally by numeral 11, is depicted in FIG. 2a. X-ray transmission is measured by x-ray module 16 which includes an x-ray source 18, preferably a linac. Other sources of x-ray radiation such as microtrons may also be used within the scope of the present invention. Source 18 sends out a beam of x-rays 19, having a specified cross-sectional profile and a maximum energy, which, for purposes of the current exposition, is assumed to be approximately 3 MeV. The cross-section of beam 19 is preferably that of a fan beam, having appreciable angular extent in only one transverse direction, however other beam cross-sectional profiles may be preferable in particular applications. X-ray beam 19 traverses an absorber 22, shown in the beam and in the FIG. 2b. The x-rays 21 pass through the absorber 22 and then traverse an inspected enclosure 10, typically a conveyance such as a cargo container or truck. Shown within enclosure 10, by way of example, is an object 14 that is readily penetrated by lower energy x-rays. Object 14 may be thin or may be composed of a light element, i.e., an element having a low atomic number Z. Object 14 is penetrated with x-rays below a few hundred keV. As an additional example, a dense object 12 is shown that cannot be effectively penetrated with the lower energy x-rays. X-rays 21 are detected in an x-ray detector 20, which is typically a segmented detector whose pitch (or segment spacing) determines the spatial resolution of the image obtained as the lateral position of incidence of beam 21 on enclosure 10 is varied by relative motion of the enclosure in direction 13 with respect to beam 21. Any motion giving rise to relative motion of enclosure 10 in direction 13 with respect to beam 21 is within the scope of the present invention, including motion of beam 21 with respect to a ground-fixed enclosure 10.

Absorber 22 is shown as a rotating cylinder. The rotation of absorber 22 may be continuous or step-wise, depending on the application. In a preferred embodiment, a first pie-pair 24 is open so that beam 19 is unattenuated as it traverses absorber 22. The term "pie-pair" is used to describe opposing segments having wedge-shaped cross-sections in a plane perpendicular to the axis of rotation of the absorber, where the axis of rotation is into the page of FIG. 2a. Other pie-pairs, shown in FIG. 2b as segments 36 and 34, are made of absorbing material. For illustration we consider the simple situation of an absorber 35 of 2 cm uranium alternating with no absorber 24. Other heavy elements, such as tungsten or lead, may also be used as absorbers. When absorber 35 is intercepting beam 19, the beam spectral profile is the filtered spectrum shown as dotted curve 8 in FIG. 1. The intensity in beam 21 of x-rays below 500 keV has been reduced by more than a factor of 10,000, while the intensity of penetrating radiation above 1.5 MeV has been reduced by only a factor of about 8.

If the pie cut-out 24 is 22.5°, then the full beam is present during ⅛ of each revolution of the absorber; the lower energy spectra, so important for inspecting lighter or thinner cargo such as 14, is being used $\frac{1}{8}^{th}$ of the time. The penetrating component of the spectrum is present all the time; $\frac{1}{8}^{th}$ of the time at full strength and $\frac{7}{8}^{th}$ of the time at about $\frac{1}{8}^{th}$ full strength.

The examples of $\frac{7}{8}^{th}$ and $\frac{1}{8}^{th}$ are illustrative, as is an absorber of 2 cm of uranium. Different absorbers and different ratios of absorber dwell times may be tailored for specific situations. Additionally, other geometries that provide for periodic interposition of an absorber 24 within the incident beam 19 are within the scope of the invention as claimed in any appended claims. FIG. 2b, for another example, shows an absorber rod in cross section which two different absorbers 34 and 36 may be used to shape the spectra for a special application of cargo inspection.

Radiation detectors 26 and 28, placed in appropriate positions at the exclusion bounds of the system (within which personnel are typically not allowed), monitor the ambient radiation and may be referred to herein as ambient radiation monitors. Only two detectors 26 and 28 are shown for illustration; in practice, detectors may be placed in as many critical positions as needed for a particular installation. Monitors 26 and 28 serve two functions: First, they control the intensity of the beam 19 emerging from the source 18. Second, they monitor the average intensity and limit that average to the specified maximum by controlling the intensity of the beams from the source 18 or sources of x-ray radiation.

A simple, effective control of the level of incident radiation is through changing the pulse rate of linac 18. In an exemplary embodiment, linac 18 emits 500 pulses per second. If cargo 10 is moved through beam 21 at 15 cm/sec and the spatial resolution of the system in the direction of motion is 0.5 cm, then the pixel is in the beam for 33 msecs. Since the linac emits 500 pulses/second, there are 16 overlapping pulses on each pixel. One or more of these pulses may be suppressed in response to a monitor signal from the ambient radiation detectors 26 and 28. This simple mechanism allows the system to vary the overall intensity by more than an order of magnitude. If a greater range of control is needed, then the intensity from the electron gun 17 of linac 18 may be modulated. In cases where a direct current or continuous wave accelerator is used in source 18 rather than a pulsed source as described heretofore, the control of the beam intensity from the accelerator is most readily accomplished by modulating the electron beam current itself, as well known in the art of x-ray generation.

The cabinet specification which prescribes the degree of shielding required for an x-ray system is typically specified in terms of an average radiation level per hour. During any given hour, many cargoes are typically examined, and generally the cargoes will vary greatly in the degree of loading. Lightly loaded trucks are generally examined effectively with an x-ray beam that produces much less radiation than the "cabinet" specification. Heavily loaded cargoes may then be examined with the maximum intensity consistent with keeping the hourly average at the "cabinet" level.

Figure 2B:
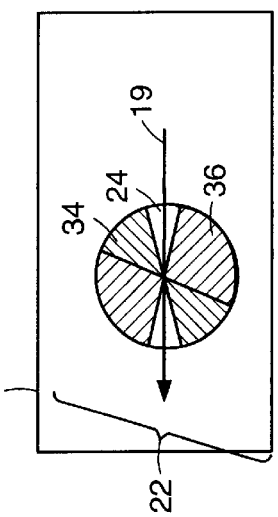
FIG. 2b shows the geometry of a rotating absorber in accordance with an embodiment of the present invention.

It should also be noted that with respect to lightly-loaded sectors of the cargo, the rotating absorber 22 described with reference to FIGS. 2a and 2b provides data for a dual-energy analysis and allows a determination of a measure of the atomic number of the objects in such lightly-loaded sectors of the cargo, as known to persons skilled in the art of x-ray inspection of cargo. Specifically, the intensity of the high-energy x-rays, detected with the absorber 35 in place, depends on the areal density of the objects but substantially not on the atomic number. The intensity with no absorber 24 can depend on the atomic number if the energy of the detected x-rays is low enough: below about 200 keV to discriminate iron and other heavy elements; below about 100 keV to discriminate at the aluminum/silicon level of atomic number.

Further refinements, in accordance with alternate embodiments of the invention, may advantageously increase the effectiveness of the inspection within the constraints of an "open cabinet" system. Such refines include, without limitation, weighing the trucks prior to inspection and arranging their position in the queue to maximize the throughput on the basis of maintaining "cabinet" status.

An unattenuated and full-powered 3 MeV beam, without special attenuator 22, penetrates almost 40 cm of iron but typically produces ambient radiation levels, at, for example, 20 feet from the fan beam, that are from two to three orders of magnitude too high for "cabinet" status. When the beam intensity is lowered, as described above, to meet the cabinet specifications, the penetration capabilities diminish to not much more than 20 cm of iron. By the means described above, combining filters and intensity control, the ambient radiation at 20 feet can be kept to "open cabinet" status and the beam will still penetrate at least 30 cm of iron. It should also be noted that the control of the intensity through the use of ambient radiation monitors 26 and 28 may advantageously allow some portion of cargoes 10 to be inspected at full power and greatest penetration.

During the dwell time at each detector 20, typically 15 ms to 30 ms, absorber 22 typically makes at least one full revolution so that the detector pixel is alternately exposed to the unattenuated beam and the attenuated beam, thereby providing two or more distinct instantaneous spectra of irradiation at different portions of the revolution of the absorber.

Radiation monitors 26 and 28 are shown at the exclusion-zone boundaries of the system, with appropriate data handling for control of the intensity of the x-ray beam by feeding their signals to a central system 30 to monitor and control the intensities of the beams 19 from the x-ray generator 18.

Figure 3:
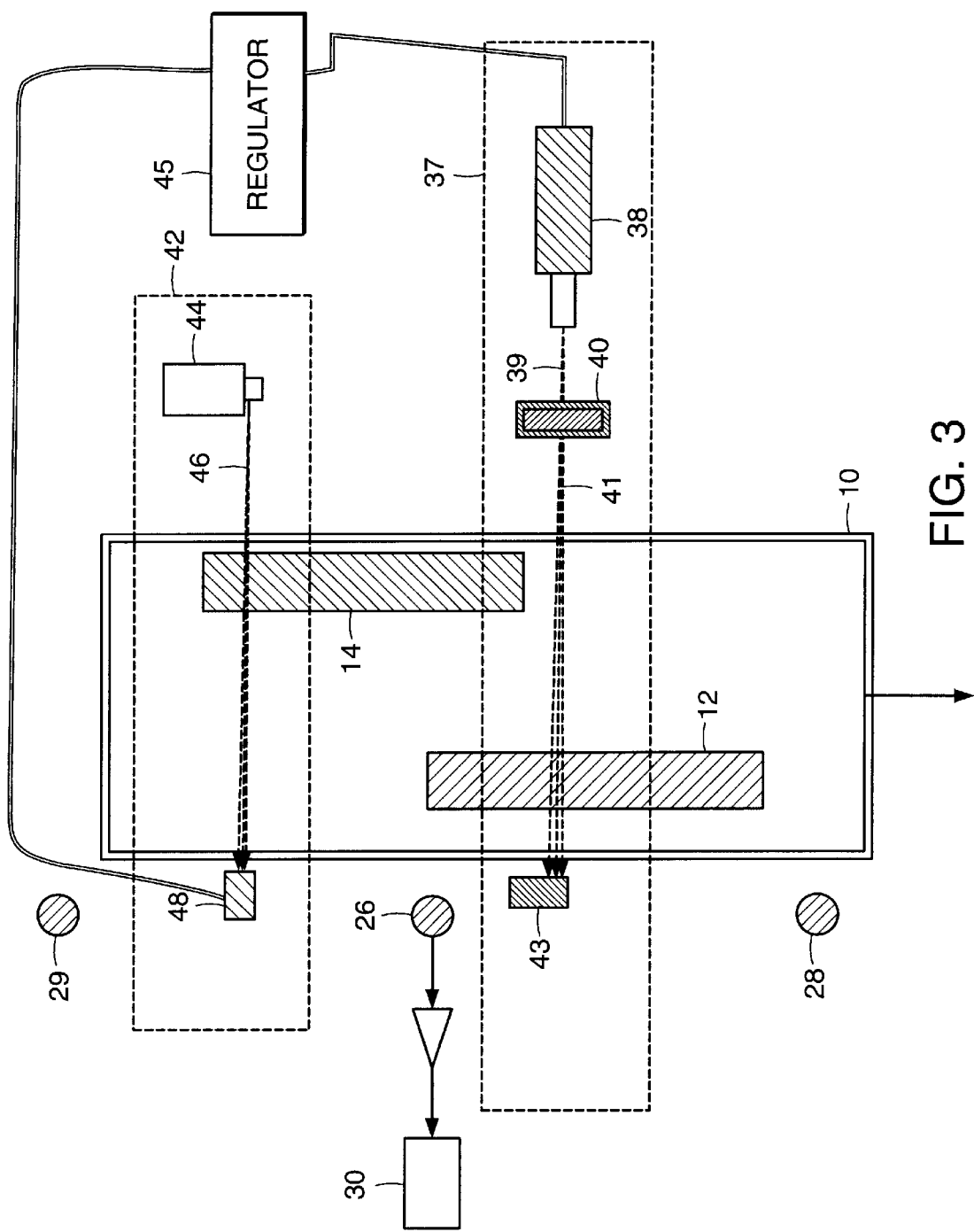
FIG. 3 is a schematic view of an x-ray inspection system using separate high- and low-energy x-ray sources in accordance with an embodiment of the current invention.

Referring now to FIG. 3, two accelerators 38 and 44 may be used, in accordance with further embodiments of the invention, to obtain two transmission images of the same container. X-ray sources 38 and 44 produce beams 39 and 46, respectively, of x-rays that may each have a specified transverse profile and that are preferably fan beams. Beams 39 and 46 are detected in detectors 43 and 48 which are preferably segmented detector arrays for use in conjunction with a fan beam geometry. System 42 in FIG. 3 is a low-energy x-ray system, which may be pulsed or not, for inspecting the lightly-loaded sections of a container with good sensitivity. The lower system 37 in the figure is a high-energy (~MeV) pulsed linac with an appropriate absorber 40 to eliminate the lower-energy x-ray components. The duty cycles of the two systems are interleaved so that only one of them is counting at any given time. Monitors of the ambient radiation 26, 28, and 29 are shown that feed their signals to a central system 30 to monitor and control the intensities of the beams from the x-ray generators, as described above with reference to FIG. 2a.

In the embodiment of the invention shown in FIG. 3, inspection by linac inspection system 37 (essentially the same as 16 in FIG. 2) is preceded by a "low-energy" inspection system 42. System 42 consists of an x-ray generator 44 in the 200 keV to 500 keV range that delivers a fan beam 46 that traverses the cargo container 10 and is detected in the segmented detector 48. System 42 uses relatively inexpensive components; for example, a standard x-ray tube 44 and detectors 48 that are many times thinner than those in array 43. The linac system 37 has been described above with reference to FIG. 2; the only difference is in the absorber 40. Absorber 40 can have several thicknesses or materials that can be inserted for maximum flexibility and control. In this preferred embodiment, we consider a single absorber of 2 cm of uranium that is always in place so that the beam 41 has the spectral intensity profile shown as the dotted curve 8 of FIG. 1. Absorber 40 is shown separate from accelerator 38. In practice, the absorber is disposed in close proximity to the accelerator anode and may be integral with it.

An important feature of this invention is that the two beams 46 from system 42, and 41 from system 37 are never detected at the same time, thus the two systems can be close together without any cross talk between them. A preferred method for implementing this feature is to make use of the fact that the linac 38 delivers beams in 2 $\mu$sec bursts that are present for only 0.1% of the time. The detector 43 is turned on just before the linac beam pulse and is shut off just afterwards. The detector 48 is turned off during the time when the x-ray beam 39 is turned on, thus preventing cross talk from the high energy system 37 into the low energy system 42. As known in the art, detector 48 may be "turned off" at many points along the electronics route, from the front end, by turning off the detector voltage, to the output end by ignoring the reading or setting to the average value of the intensities preceding and following the linac pulse. Preventing cross talk in either direction is trivial if the x-ray generator 44 is a pulsed accelerator since its pulses can be interleaved with those of 38. If, as is preferred, the accelerator 44 is a direct current x-ray tube, then the beam 46 should be switch off during the brief periods when beam 39 is on. The ability to switch the beam current 46 on and off in microseconds is built into many commercially available x-ray generators.

The x-ray system 42 serves two primary functions: First, it produces a transmission image through the lightly-loaded components of the cargo using the low-energy x-rays necessary for high sensitivity. Second, its image of any section of the cargo 10 is obtained many seconds before the corresponding section is inspected by system 37 so that the results obtained from the image of system 42 can automatically, by means of regulator 45, control the intensity of the beam from the accelerator 38. For example, the light object 14 in FIG. 3, need not be examined at all with system 37, which needs to be on only to examine the dense object 12. Since object 12 only occupies about half the length of the container 10, the power of the accelerator 38 can be increased by a factor of two during the on time, to obtain greater penetration. As other examples, if stowaways are discovered by use of the low-energy beam, the high-energy beam should be shut off. Similarly, if foodstuffs are discovered, then the energy of the linac should be shifted to 500 keV to comply with standards for food irradiation.

The results obtained from the image from system 42 can also be used to control the angular distribution of the fan beam 41. To do so, absorber 40 is articulated in the vertical direction. Each articulated segment has a plurality of positions and may be controlled by computer: a nominal absorber such as the 2 cm thickness of uranium is inserted to inspect thick objects and a very thick, "black" absorber is inserted at the height positions that have already been inspected by the low energies of system 42. Operating in this manner, absorber 40 acts as a beam profile shaper of fan beam 41.

Ambient radiation detectors 26, 28, and 29 serve the same functions in this embodiment as they did in the embodiment described above with reference to FIG. 2a. Additionally, ambient radiation detectors 26, 28, and 29 advantageously maintain the maximum effectiveness of the low and high energy components.

Figure 4:
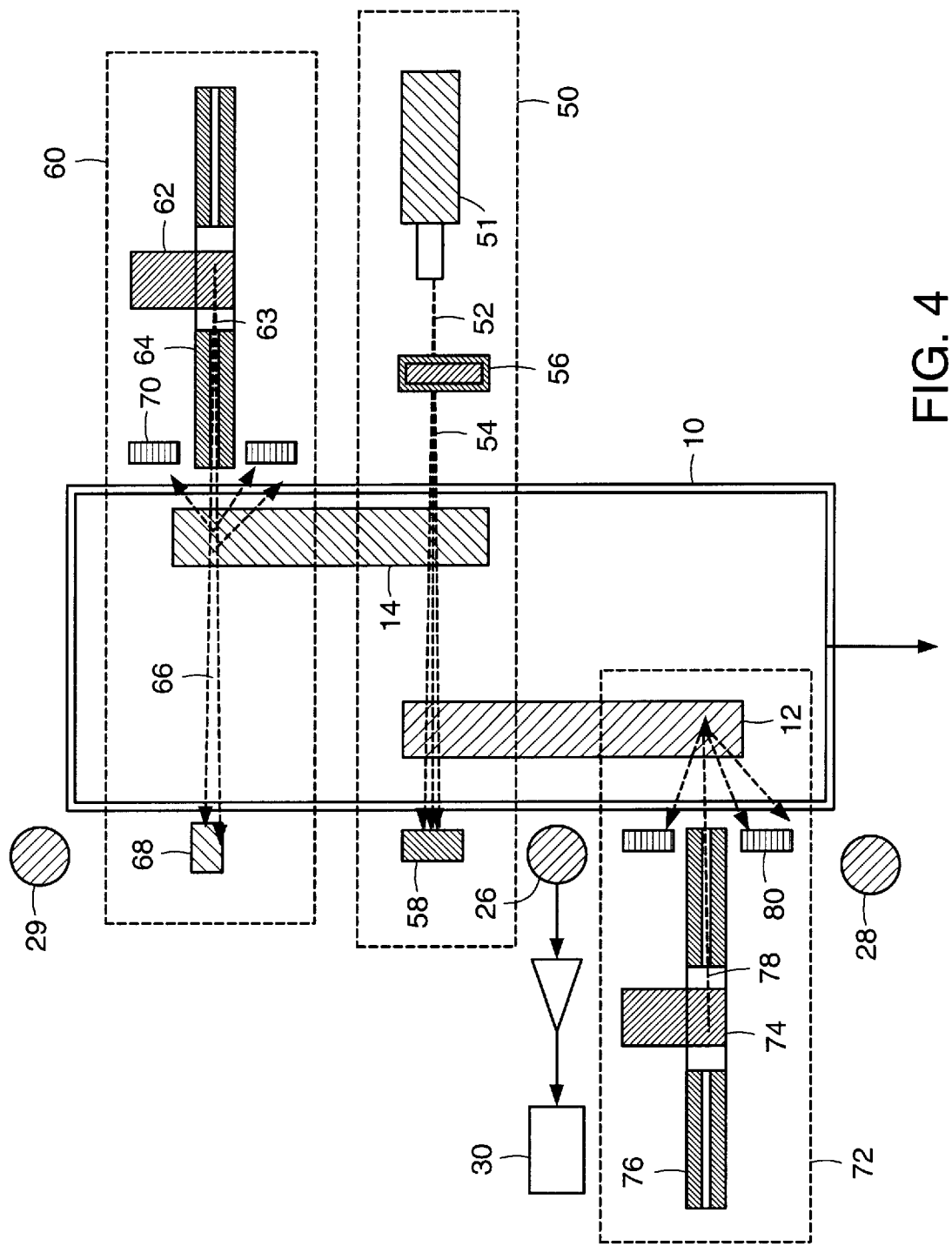
FIG. 4 is a schematic of a cargo inspection system showing two independent backscatter systems and a separate high-energy transmission system and monitors of the ambient radiation in accordance with a preferred embodiment of the present invention.

Referring now to FIG. 4, a schematic is shown of an embodiment of the invention in which backscatter images are obtained from two sides of the cargo 10 by systems 60 and 72. Each of systems 60 and 72 consists of an x-ray tube 62 and 74 operating at a typical maximum energy of approximately 440 keV, though other operating voltages as low as 200 keV may be appropriate, depending on the application. The generated x-rays 63 and 78 are formed into a sweeping pencil beam by rotating wheels 64 and 76, each having hollow spokes. A typical chopper wheel may have 4 spokes spaced 90° apart so that a pencil beam sweeps through the cargo four times per revolution. X-rays transmitted through cargo 10 are detected in an unsegmented detector 68. X-rays backscattered from objects such as 14 are detected in backscatter detectors 70 and 80.

The transmission image of system 60 serves the same functions as the transmission system 42 served in the embodiment described above with reference to FIG. 3: it produces the necessary image of the lightly loaded sections of the cargo and it controls the on-time intensity of the x-ray beam from the linac system 50.

The lower energy x-ray system 72 need only be a backscatter system since the necessary transmission images have been obtained from systems 60 and 50.

Cross talk among the three systems 60, 50, and 72 may be minimized in different ways within the scope of the invention. It may be assumed, for sake of the following example and without limitation, that system 50 uses the 3 MeV pulsed linac and that systems 60 and 72 use direct current x-ray tubes. To prevent cross talk between the linac and the direct current accelerators, detectors 68, 70, and 80, and the beams 63 and 78 are all turned off when the beam 52 is on. Turning off the beams in systems 60 and 72, and blanking detectors 68, 70 and 80 creates small, easily corrected artifacts since only about a single pixel in a thousand is affected. The cross talk between the systems 60 and 72 will generally be small since they are relatively far apart, but to completely eliminate that cross talk it is only necessary to interleave the scanning pencil beams. For example, the wheels 64 and 76 may each have only two spokes; the former at say 0° and 180°, the latter at 90° and 270°. As the synchronized wheels rotate, the beams incident upon cargo 10 alternate. In this method, the wheels rotate at twice the speed that would be required if each had 4 spokes.

Referring further to FIG. 4, ambient radiation monitors 26, 28, and 29, as above, control the intensities from the accelerators so that the ambient radiation levels meet but never exceed the "cabinet" specifications. This embodiment may be especially advantageous in that it adds imaging through heavily loaded cargo without increasing the cost of the infrastructure in any significant way. Detailed Monte Carlo simulations show that the system shown schematically in FIG. 4 can image through more than 30 cm of steel for all cargo while retaining the "open cabinet" specifications in a 40 foot drive-through passage (the typical length of a semi-trailer) without the need for doors or a roof for the containment of the ionizing radiation. Little shielding or radiation-containing infrastructure is needed to meet the radiation safety standards of a "open cabinet" designation, thereby saving the customer millions of dollars in building costs, an important factor in marketing these systems.

Embodiments of the present invention may advantageously be applied such that MeV systems may have both high sensitivity to thin objects using low energy x-rays and high penetration of thick objects using high energy x-rays and do so with an open inspection structure that maintains "open cabinet" status. It should be emphasized that an "open" inspection structure may have a roof and doors but these would not be for radiation shielding.

This invention shows how, in several different x-ray systems, the radiation field can be minimized so that the inspection systems can be "open cabinet", while maintaining both the high-energy and low-energy x-ray capabilities. The former spectrum is formed by means of absorbers. Further gains are made by using ambient radiation monitors to control the intensity of the beams from the x-ray generators and maintain the most effective sensitivity and penetration, while keeping within "open cabinet" specifications.

An alternative embodiment to the embodiment described with reference to FIG. 4 omits transmission detector 68 from system 60 and uses the method described with reference to FIG. 2 with its variable absorber 22. This variation on the basic theme lacks the flexibility of the embodiment shown in FIG. 4 but may be used advantageously in situations where it is appropriate to use x-ray energies of quite low energy, say below 150 keV, in the backscatter systems 60 and 72.

For purposes of the examples described above, it may be assumed, without limitation, that the high energy accelerator is a pulsed, 3 MeV linear accelerator (linac) that delivers x-rays in 2 $\mu$s bursts spaced 2 ms apart; i.e., 500 pulses per second and a duty factor of $10^{-3}$. Indeed, accelerators, delivering up to kilowatts of average power, are commercially available with energies from less then 2 MeV to more than 9 MeV.

It should be noted, in accordance with an alternate embodiment of the invention, that different absorbers may be selected for each accelerator energy so as to shape the resultant energy spectrum for maximum penetration consistent with the type of contents of the inspected container and a maximum specified ambient dose or specified average dose.

While the invention has been described in detail, it is to be clearly understood that the same is by way of illustration and example and is not to be taken by way of limitation. Indeed, numerous variations and modifications will be apparent to those skilled in the art. All such variations and modifications are intended to be within the scope of the present invention as defined in the appended claims.

We claim:

1. An inspection system for inspecting an object, the inspection device comprising:
   a. a source of penetrating radiation for generating a beam and for irradiating the object, the source characterized at each instant of time by an instantaneous energy spectrum and an intensity;
   b. at least one detector for detecting the penetrating radiation after interaction with the object; and
   c. a regulator for providing incident penetrating radiation having a first instantaneous spectrum dominated by photons of energies less than a first fiducial energy in a first instance wherein photons of energies less than the first fiducial energy penetrate through the object, the regulator providing incident penetrating radiation having a second instantaneous spectrum dominated by photons of energies exceeding a second fiducial energy in a second instance wherein photons of energies less than the first fiducial energy do not penetrate through the object, such that an average radiation dose is maintained below a specified level.

2. An inspection system according to claim 1, wherein the source of penetrating radiation includes a time-variable filter.

3. An inspection system according to claim 2, wherein the time-variable filter is a rotating element having a plurality of segments of distinct spectral absorption characteristics.

4. An inspection system according to claim 3, wherein each of the plurality of segments has a wedge-shaped cross-section.

5. An inspection system according to claim 2, wherein the time-variable filter includes an absorber chosen from the group of heavy elements including uranium, tungsten, and lead.

6. An inspection system according to claim 1, further comprising:
   a. at least one ambient radiation monitor for creating a signal based on radiation detected outside an exclusion zone; and
   b. a controller for regulating the intensity of the source based at least on the signal.

7. An inspection system according to claim 6, wherein the source is pulsed and the controller regulates the number of beam pulses per unit time based at least on the signal.

8. A method for inspecting an object, the method comprising:
   a. generating a beam of penetrating radiation characterized at each instant of time by an instantaneous energy spectrum and an intensity;
   b. irradiating a portion of the object, up to the entirety thereof, with the beam;
   c. detecting the penetrating radiation after interaction with the object; and
   d. modulating the incident penetrating radiation in such a manner as to provide an instantaneous spectrum dominated by photons of energies less than a first fiducial energy unless the photons of energies less than the first fiducial energy fail to penetrate through the object, in which case
   e. modulating the incident penetrating radiation in such a manner as to change the instantaneous energy spectrum to provide a second instantaneous spectrum dominated by photons of energies exceeding a second fiducial energy such that an average radiation dose is maintained below a specified level.

* * * * *